(12) United States Patent
Hwang et al.

(10) Patent No.: US 12,412,661 B2
(45) Date of Patent: Sep. 9, 2025

(54) ELECTRONIC DEVICE AND METHOD OF PROVIDING HEALTH GUIDELINE USING THE SAME

(71) Applicant: SAMSUNG ELECTRONICS CO., LTD., Suwon-si (KR)

(72) Inventors: Jeong Eun Hwang, Suwon-si (KR); Jin Young Park, Hwaseong-si (KR); Yoon Jae Kim, Seoul (KR); Hyun Seok Moon, Hwaseong-si (KR); Kun Sun Eom, Yongin-si (KR); Myoung Hoon Jung, Bucheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 308 days.

(21) Appl. No.: 17/706,073

(22) Filed: Mar. 28, 2022

(65) Prior Publication Data

US 2023/0162856 A1 May 25, 2023

(30) Foreign Application Priority Data

Nov. 25, 2021 (KR) .................. 10-2021-0164966
Dec. 23, 2021 (KR) .................. 10-2021-0186103

(51) Int. Cl.
*G16H 50/20* (2018.01)
*G16H 20/30* (2018.01)
(Continued)

(52) U.S. Cl.
CPC ............. *G16H 50/20* (2018.01); *G16H 20/30* (2018.01); *G16H 20/60* (2018.01); *G16H 40/67* (2018.01)

(58) Field of Classification Search
CPC ........ G16H 50/20; G16H 20/30; G16H 20/60; G16H 40/67; G16H 50/30
(Continued)

(56) References Cited

U.S. PATENT DOCUMENTS 6,612,382 B2   9/2003   King
7,842,471 B2   11/2010  Lee et al.
(Continued)

FOREIGN PATENT DOCUMENTS

KR   10-2009-0014811 A   2/2009
KR   10-2012-0012364 A   2/2012
(Continued)

OTHER PUBLICATIONS

Palafox-Carlos, The Role of Dietary Fiber in the Bioaccessibility and Bioavailability of Fruit and Vegetable Antioxidants, 2011, Journal of Food Science, 76, 1 (Year: 2011).*
(Continued)

*Primary Examiner* — Kambiz Abdi
*Assistant Examiner* — Tran N Nguyen
(74) *Attorney, Agent, or Firm* — Sughrue Mion, PLLC

(57) ABSTRACT

An electronic device for providing a health guideline is provided. The electronic device may include a main body, an optical sensor disposed on a first surface of the main body and configured to measure a light signal from an object; a display disposed on a second surface of the main body; and a processor configured to obtain a concentration of an antioxidant component of a user based on the light signal, obtain a utilization rate of the antioxidant component using personal information of the user that is associated with the concentration of the antioxidant component, and provide a guideline to the user through the display based on the utilization rate of the antioxidant component.

18 Claims, 16 Drawing Sheets

(51) Int. Cl.
    *G16H 20/60*     (2018.01)
    *G16H 40/67*     (2018.01)

(58) Field of Classification Search
    USPC .......................................................... 705/2–3
    See application file for complete search history.

(56) References Cited

U.S. PATENT DOCUMENTS

| | | | |
|---|---|---|---|
| 8,116,842 | B2 | 2/2012 | Fralick et al. |
| 8,260,402 | B2* | 9/2012 | Ermakov ............... G01N 21/65 600/335 |
| 9,247,884 | B2 | 2/2016 | Yuen et al. |
| 10,004,406 | B2 | 6/2018 | Yuen et al. |
| 10,627,783 | B2 | 4/2020 | Rothkopf et al. |
| 2003/0208113 | A1* | 11/2003 | Mault .................... G16H 40/63 600/316 |
| 2013/0085079 | A1 | 4/2013 | Gill et al. |
| 2015/0168423 | A1 | 6/2015 | Gill et al. |
| 2017/0108433 | A1* | 4/2017 | Helfmann .......... G01N 21/4785 |
| 2018/0260954 | A1* | 9/2018 | Jung ................... G06F 18/2413 |
| 2018/0344259 | A1* | 12/2018 | Pavlov ............... A61B 5/14532 |
| 2019/0150746 | A1* | 5/2019 | Kim ..................... A61B 5/6824 |
| 2020/0013490 | A1* | 1/2020 | Rumoro ................ G16H 10/60 |
| 2020/0041342 | A1* | 2/2020 | Jang ....................... G01N 21/59 |
| 2020/0166523 | A1 | 5/2020 | Gill et al. |
| 2020/0201657 | A1 | 6/2020 | Kang |
| 2020/0335185 | A1* | 10/2020 | Martin .................. G16H 10/60 |
| 2020/0352478 | A1 | 11/2020 | Park |
| 2020/0378890 | A1* | 12/2020 | Lee .................... G01N 21/3577 |
| 2021/0057104 | A1* | 2/2021 | Krebs .................. A61B 5/0044 |
| 2021/0142905 | A1 | 5/2021 | Segal et al. |

FOREIGN PATENT DOCUMENTS

| | | |
|---|---|---|
| KR | 10-2015-0026166 A | 3/2015 |
| KR | 10-2015-0106491 A | 9/2015 |
| KR | 10-2017-0054628 A | 5/2017 |
| KR | 10-2019-0019397 A | 2/2019 |
| KR | 10-2033063 B1 | 10/2019 |
| KR | 10-2020-0055804 A | 5/2020 |
| KR | 10-2020-0084383 A | 7/2020 |
| KR | 10-2020-0129409 A | 11/2020 |

OTHER PUBLICATIONS

Heikenfeld, Wearable sensors: modalities, challenges, and prospects, 2018, Lab Chip, 18, 217-248 (Year: 2018).*

Jahns, Concurrent validity of skin carotenoid status as a concentration biomarker of vegetable and fruit intake compared to multiple 24-h recalls and plasma carotenoid concentrations across one year: a cohort study, 2019, Nutr J 18, 78 (Year: 2019).*

Jahns, Concurrent validity of skin carotenoid status as a concentration biomarker of vegetable and fruit intake compared to multiple 24-h recalls and plasma carotenoid concentrations across one year: a cohort study, 2019, Nutr J 18, 78 (Year: 2019) (Year: 2019).*

Fernandez-Garcia et al., "Carotenoids bioavailability from foods: From plant pigments to efficient biological activities," Food research international, vol. 46, No. 2, pp. 438-450, 2012, Abstract, total 2 pages.

Tremblay et al., "Weighted gene co-expression network analysis to explain the relationship between plasma total carotenoids and lipid profile," Genes & Nutrition, vol. 14, No. 16, 2019, total 12 pages.

Vohl et al., "Editorial: Dietary Factors, Epigenetics and Their Implications for Human Obesity," Frontiers in Endocrinology, vol. 11, No. 601, Aug. 2020, total 3 pages.

Zeevi et al., "Personalized Nutrition by Prediction of Glycemic Responses," Cell, vol. 163, pp. 1079-1094, Nov. 2015, total 17 pages.

Borel, "Genetic variations involved in interindividual variability in carotenoid status," Molecular Nutrition and Food Research, Wiley-VCH Verlag, vol. 56, No. 2, 2012, total 37 pages.

Tan et al., "Carotenoids: How Effective Are They to Prevent Age-Related Diseases?," Molecules, vol. 24, No. 1801, 2019, total 23 pages.

Massenti et al., "Regular consumption of fresh orange juice increases human skin carotenoid content," International Journal of Food Sciences and Nutrition, Aug. 2015, total 14 pages.

Lietz et al., "From carotenoid intake to carotenoid blood and tissue concentrations—implications for dietary intake recommendations," Nutrition Reviews, May 2021, total 31 pages.

Kolodziejczyk et al., "Diet-microbiota interactions and personalized nutrition," Nature Reviews, Microbiology, 2019, total 12 pages.

Bar et al., "A reference map of potential determinants for the human serum metabolome," Nature, 2020, total 28 pages.

* cited by examiner

ELECTRONIC DEVICE AND METHOD OF PROVIDING HEALTH GUIDELINE USING THE SAME

CROSS-REFERENCE TO RELATED APPLICATION(S)

This application claims the benefit under 35 USC § 119(a) of Korean Patent Application No. 10-2021-0164966, filed on Nov. 25, 2021 and Korean Patent Application No. 10-2021-0186103, filed on Dec. 23, 2021 in the Korean Intellectual Property Office, the disclosures of which are incorporated herein by reference in their entireties.

BACKGROUND

1. Field

Apparatuses and methods consistent with example embodiments relate relates to providing health guidelines via an electronic device.

2. Description of Related Art

Reactive oxygen species are an important part of the biological defense mechanisms, such as white blood cells that protect the body against infections. However, it has been known that excessive production of reactive oxygen species in the body may lead to various diseases in tissues. Common factors that cause the reactive oxygen species include stress, alcohol, peroxides, medicine, and the like. The reactive oxygen species produced by these factors may cause cranial nerve diseases, circulatory diseases, cancer, digestive tract diseases, liver diseases, arteriosclerosis, renal diseases, diabetes, aging, and the like. Human bodies have a series of antioxidant defense systems to protect against oxygen toxicity. In order for such systems to normally operate, it is essential to have sufficient amounts of antioxidants such as vitamin E, vitamin C, carotenoid, flavonoid, ascorbic acid, tocopherol, and the like, and it is important to consume a sufficient amount of foods that are rich in antioxidants for an effective antioxidant action. Thus, there is a growing need for an apparatus for providing personalized health guidelines reflecting individual's characteristics, focusing on antioxidants, for overall health management of individuals.

SUMMARY

According to an aspect of the present disclosure, there is provided an electronic device including: a main body; an optical sensor disposed on a first surface of the main body and configured to measure a light signal from an object; a display disposed on a second surface of the main body; and a processor configured to obtain a concentration of an antioxidant component of a user based on the light signal, obtain a utilization rate of the antioxidant component using personal information of the user that is associated with the concentration of the antioxidant component, and provide a guideline to the user through the display based on the utilization rate of the antioxidant component.

The optical sensor may include a light source configured to emit light to the object and a detector configured to detect light reflected or scattered by the object.

The personal information may include at least one of genetic information, clinical information, physiological pattern information, or body information of the user, the genetic information may include a gene associated with the concentration of the antioxidant component, the clinical information may include gut microbial information, the physiological pattern information may include at least one of stress, exercise amount, sleep pattern, alcohol consumption, or smoking amount, and the body information may include at least one of gender, age, height, weight, or body composition.

The processor may be further configured to select the personal information associated with the concentration of the antioxidant component by using a machine learning method.

The processor may be further configured to output an interface to the display to receive a direct input of the personal information associated with the concentration of the antioxidant component from the user, collect the personal information in conjunction with a health application installed in the electronic device, or collect the personal information from another electronic device.

The processor may be further configured to obtain the utilization rate of the antioxidant component based on at least one of an absorption rate or an amount of consumption of the antioxidant component by using the personal information.

The processor may be further configured to determine the absorption rate of the antioxidant component based on at least one of gut microorganisms, genes, or proteins, and determine the amount of consumption of the antioxidant component based on at least one of physiological pattern information or body information.

The processor may be further configured to determine a user grade corresponding to the utilization rate of the antioxidant component, and provide a health guideline to the user through the display according to the user grade.

The processor may be further configured to classify a user type according to the user grade and output, as the health guideline, at least one of a diet suggestion and a life pattern suggestion through the display according to the user type.

The diet suggestion may include at least one of a nutritional supplement or a user-customized diet, and the life pattern suggestion includes at least one of an exercise amount, a sleep pattern, or a meal time.

The processor may be further configured to further obtain a required amount of the antioxidant component by using the personal information, and provide a health guideline to the user based on the utilization rate of the antioxidant component and the required amount of the antioxidant component.

According to another aspect of the present disclosure, there is provided a method of providing a guideline, the method including: measuring a light signal from an object; obtaining a concentration of an antioxidant component based on the measured light signal; obtaining a utilization rate of the antioxidant component by using personal information of a user that is associated with the concentration of the antioxidant component; and providing a health guideline to the user based on the utilization rate of the antioxidant component.

The personal information associated with the concentration of the antioxidant component may include at least one of genetic information, clinical information, physiological pattern information, or body information of the user, the genetic information may include a gene associated with the concentration of the antioxidant component, the clinical information includes gut microbial information, the physiological pattern information may include at least one of stress, exercise amount, sleep pattern, alcohol consumption, or smoking amount, and the body information may include at least one of gender, age, height, weight, or body composition.

The obtaining of the utilization rate of the antioxidant component may include selecting the personal information associated with the concentration of the antioxidants component by using a machine learning method.

The obtaining of the utilization rate of the antioxidant component may include receiving a direct input of the personal information associated with the concentration of the antioxidant component from the user, collecting the personal information in conjunction with a health application installed in the electronic device, or collecting the user's personal information from another electronic device.

The obtaining of the utilization rate of the antioxidant component may include obtaining the utilization rate of the antioxidant component based on at least one of an absorption rate or an amount of consumption of the antioxidant component by using the personal information.

The absorption rate of the antioxidant component may be determined based on at least one of gut microorganisms, genes, or proteins, and the amount of consumption of the antioxidant component is determined based on at least one of physiological pattern information or body information.

The providing of the health guideline to the user may include determining a user grade corresponding to the utilization rate of the antioxidant component and providing the health guideline to the user through a display according to the user grade.

The providing of the health guideline to the user may include classifying a user type according to the user grade, and outputting, as the health guideline, at least one of a diet suggestion and a life pattern suggestion through the display according to the user type.

According to another aspect of the present disclosure, there is provided a non-transitory computer-readable storage medium storing a program that is executable by a computer to perform a method of providing dietary guidelines, the method including: obtaining an optical signal from an object using an antioxidant sensor; inputting the optical signal to a machine learning model that is trained to predict a carotenoid concentration based on input parameters that reflect an amount of food consumption, an age, and a weight of a user; identify antioxidant level changes of the user based on an output signal of the machine learning model; and provide the dietary guidelines based on the antioxidant level changes of the user.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
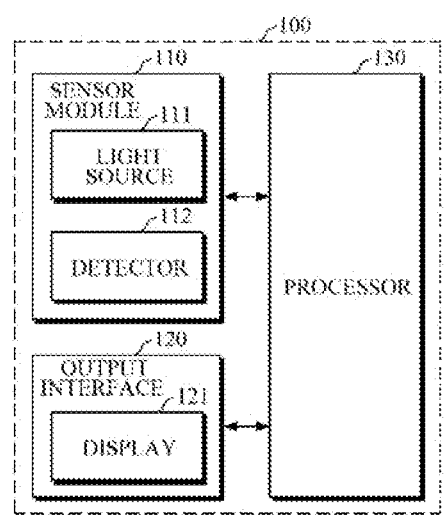
FIG. 1 is a block diagram illustrating an electronic device according to an exemplary embodiment.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising," will be understood to imply the inclusion of stated elements but not the exclusion of any other elements. Terms such as "unit" and "module" denote units that process at least one function or operation, and they may be implemented by using hardware, software, or a combination of hardware and software.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

An electronic device according to various embodiments of this disclosure may include at least one of, for example, smartphones, tablet personal computers (PCs), mobile phones, video telephones, electronic book readers, desktop PCs, laptop PCs, netbook computers, workstations, servers, personal digital assistants (PDAs), portable multimedia players (PMPs), Motion Picture Experts Group (MPEG-1 or MPEG-2) Audio Layer 3 (MP3) players, mobile medical devices, cameras, or wearable devices. According to various embodiments, the wearable device may include at least one of an accessory type (e.g., watches, rings, bracelets, anklets, necklaces, glasses, contact lens, or head-mounted-devices (HMDs)), a fabric or garment-integrated type (e.g., an electronic apparel), a body-attached type (e.g., a skin pad or tattoos), or a bio-implantable type (e.g., an implantable circuit). According to another embodiment, an electronic device may include at least one of various medical devices (e.g., various portable medical measurement devices (e.g., a blood glucose monitoring device, a heartbeat measuring device, a blood pressure measuring device, a body temperature measuring device, and the like), a magnetic resonance angiography (MRA), a magnetic resonance imaging (MRI), a computed tomography (CT), scanners, and ultrasonic devices), navigation devices, Global Navigation Satellite System (GNSS), event data recorders (EDRs), flight data recorders (FDRs), vehicle infotainment devices, electronic equipment for vessels (e.g., navigation systems and gyrocompasses), avionics, security devices, head units for vehicles, industrial or home robots, automatic teller's machines (ATMs), points of sales (POSs) of stores, or internet of things (e.g., light bulbs, various sensors, electric or gas meters, sprinkler devices, fire alarms, thermostats, street lamps, toasters, exercise equipment, hot water tanks, heaters, boilers, and the like). Furthermore, an electronic device according to an embodiment of this disclosure may not be limited to the above-described electronic devices and may include other electronic devices and new electronic devices according to the development of technologies.

FIG. 1 is a block diagram illustrating an electronic device according to an exemplary embodiment.

Referring to FIG. 1, an electronic device 100 may include a sensor module 110, an output interface 120, and a processor 130. The sensor module 110 may be disposed on one surface (e.g., the rear surface) of a main body of the electronic device 100, and the display 121 may be disposed on the other surface (e.g., the front surface) of the electronic device 100.

The sensor module (e.g., an optical sensor or an optical antioxidant sensor) 110 may include a light source 111 configured to emit light to an object, and a detector 112 configured to detect light reflected or scattered by the object.

The light source 111 may include a light emitting diode (LED), a laser diode, and a phosphor. One or more light sources may be provided, and each light source may emit light of the same wavelength or light of different wavelengths (e.g., a red wavelength, a green wavelength, a blue wavelength, an infrared wavelength, etc.). For example, a measurement wavelength range may be from 400 nm to 600 nm. The detector 112 may include a photodiode, a phototransistor, a complementary metal oxide semiconductor (CMOS) image sensor, a charge-coupled device (CCD) image sensor, and the like, and may be configured as a single detector, a plurality of detectors, or a detector array. The plurality of detectors or the detector array may be arranged in a predetermined shape, for example, a concentric circle, a rectangle, a triangle, or the like, around the light source 111.

Figure 2:
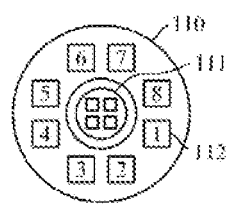
FIG. 2 illustrates a structure of a sensor module according to an exemplary embodiment.

FIG. 2 illustrates a structure of a sensor module 10 according to an exemplary embodiment. For example, the structure of the sensor module 110 of FIG. 2 may correspond to a rear surface of a smart watch-type wearable device. Referring to FIG. 2, a light source 111 is disposed at the center of the sensor module 110, and a plurality of detectors 112 may be disposed in a concentric circle shape on the outer side of the light source 111. Although eight detectors 112 are shown in FIG. 2, the present disclosure is not limited thereto.

Referring back to FIG. 1, the output interface 120 may output data generated or processed by the electronic device 100 in a visual/non-visual manner. The output interface 120 includes a display 121, and may include other sound output interfaces, audio modules, and/or haptic modules which are not shown herein.

The display 121 may visually provide information external to the electronic device 100. The display 121 may include a display, a hologram device, or a projector, and control circuitry to control a corresponding device. The display 121 may include touch circuitry adapted to detect a touch, or sensor circuitry (e.g., a pressure sensor) adapted to measure an intensity of force incurred by the touch.

The sound output interface may output a sound signal external to the electronic device 100. The sound output interface may include a speaker and/or a receiver. The speaker may be used for general purposes, such as playing multimedia or playing record, and the receiver may be used for an incoming calls. The receiver may be combined as part of the speaker or may be implemented as an independent separate device.

The audio module may convert sound into an electric signal or inversely convert an electric signal into sound. The audio module may obtain sound through an input device, and may output sound through the sound output interface and/or a speaker and/or a headphone of another electronic device directly or wirelessly connected to the electronic device.

The haptic module may convert an electrical signal into a mechanical stimulus (e.g., a vibration or a movement) or electrical stimulus which may be recognized by a user via his tactile sensation or kinesthetic sensation. The haptic module may include a motor, a piezoelectric element, and/or an electric stimulator.

The processor 130 may be electrically or wirelessly connected to various components in the electronic device 100, such as the sensor module 110, the output interface 120, and the like, to control the components and perform various data processing or calculations.

For example, the processor 130 may control the sensor module 110 to obtain bio-information by using light amount data obtained by the detector 112 of the sensor module 110. In this case, the bio-information may be the concentration of an antioxidant component including the concentration of carotenoids accumulated in the skin. However, this is merely an example, and the bio-information may include various information, such as blood sugar, triglyceride, alcohol, lactate, pigment in the skin, blood flow rate, and the like.

When the sensor module 110 completes the measurement, the processor 130 may calculate absorbance at each wavelength based on a ratio between the measured amount of light and a reference amount of light, and extract a feature value using the absorbance at each wavelength. For example, the feature value may be extracted by combining the calculated absorbance at each wavelength and correcting the baseline of a waveform. Bio-information may be obtained by applying the obtained feature value to a predefined estimation model. Equations 1 to 3 below show an example of calculating the absorbance at each wavelength and determining a value of the concentration of an antioxidant component using the calculated absorbance at each wavelength.

$$A(\lambda) = -\log_{10}\frac{I_m}{I_0} \quad (1)$$

Here, $A(\lambda)$ represents the absorbance at each wavelength, $I_m$ represents the amount of light of a specific wavelength measured at a first region of the object, and $I_0$ represents the reference amount of light obtained as a result of calibration for the specific wavelength.

$$AO = A_{\lambda 2} - \left(\frac{\lambda_3 - \lambda_2}{\lambda_3 - \lambda_1}\right) \times A_{\lambda 1} - \left(\frac{\lambda_2 - \lambda_1}{\lambda_3 - \lambda_1}\right) \times A_{\lambda 3} \quad (2)$$

Here, AO is an example of a feature value and represents an antioxidant peak obtained by combining the wavelength-specific absorbance and correcting the baseline of a waveform. $\lambda_1$, $\lambda_2$, and $\lambda_3$ each represent a wavelength, and $A_{\lambda 1}$, $A_{\lambda 2}$, and $A_{\lambda 3}$ each represent absorbance at each wavelength obtained through Equation 1. The length of the wavelength may be longer in order of $\lambda_1$, $\lambda_2$, and $\lambda_3$.

$$Y = a \times AO + b \quad \text{[Equation 3]}$$

Here, Y represent a value of antioxidant concentration, AO represents an antioxidant peak, and a and b represent preset values. However, Equation 3 shows an example of an antioxidant concentration value estimation model defined as a linear function, but is not limited thereto, and may be defined as a non-linear function, such as a logarithmic function, an exponential function, or the like.

The processor 130 may provide a health guideline to the user based on the acquired concentration of the antioxidant component and user's personal information.

In general, blood is used to estimate the concentration of an antioxidant component in a living body and to determine an individual's health status, but this is an invasive method. In addition, when only the concentration in blood is used, differences in individual's characteristics such as genetic, physical, and physiological patterns may not be reflected. Therefore, there is a need for a method of non-invasively obtaining the concentration of an antioxidant component using an optical sensor or the like, and providing a personalized health guideline in which the obtained concentration of the antioxidant component and the corresponding individual's characteristics are reflected.

For example, the processor 130 may obtain the rate of utilization of the antioxidant component by using the user's personal information associated with the concentration of the antioxidant component.

In this case, the user's personal information associated with an antioxidant component may be various types of information indicating the characteristics of the user, for example, genetic information, clinical information, physiological pattern information, or body information of the user. For example, the genetic information may include genes associated with the concentration of an antioxidant component, the clinical information may include gut microbial information and disease information, the physiological pattern information may include stress, exercise amount, sleep pattern, alcohol consumption, or smoking amount, and the body information may include gender, age, height, weight, or body composition. However, the present disclosure is not limited thereto.

The user's genetic information may vary depending on an individual's diet, and individuals may differ in absorption, assimilation, distribution, metabolism, and excretion of antioxidant components (e.g., carotenoids). Table 1 below shows examples of user genetic information associated with antioxidant components, but the present disclosure is not limited thereto.

TABLE 1

| Genes | Vitamin A conversion gene | BCO1(BCMO1) |
|---|---|---|
| | Vitamin A transport gene | TTR |
| | Vitamin A transport gene | FFAR4(RBP4) |
| | Vitamin A catalytic gene | PKD1L2(BCMO1) |

The clinical information may be information that can be obtained from health checkup or medical record, and may include, for example, gut microbial information. Gut microbial information is related to the metabolism of antioxidant components according to individual diet. Types of gut microorganisms associated with the concentration of an antioxidant component may include *Akkermansia muciniphila*, *Lactobacillus* spp., *Bifidobacterium* spp., *Alistipes* spp., etc., but are not limited thereto. Also, the clinical information may also include an individual's disease information. For example, if a user has is a disease such as obesity, diabetes, surgery experience, cancer, etc., the concentration of antioxidant components of the user tends to decrease.

The physiological pattern information may include stress level, exercise amount, sleep pattern, drinking amount, or smoking amount. In general, in the cases of high stress level, excessive exercise, irregular sleep patterns, smokers, and alcohol drinkers, the concentration of antioxidant components tends to decrease.

The body information may include gender, age, height, weight, or body mass index. In general, in the cases of men, older age groups, people with large height, people with high weight, and people with high body mass index, the concentration of antioxidant components tends to be low.

The processor 130 may select the user's personal information associated with the antioxidant component using a machine learning method.

Figure 3A:
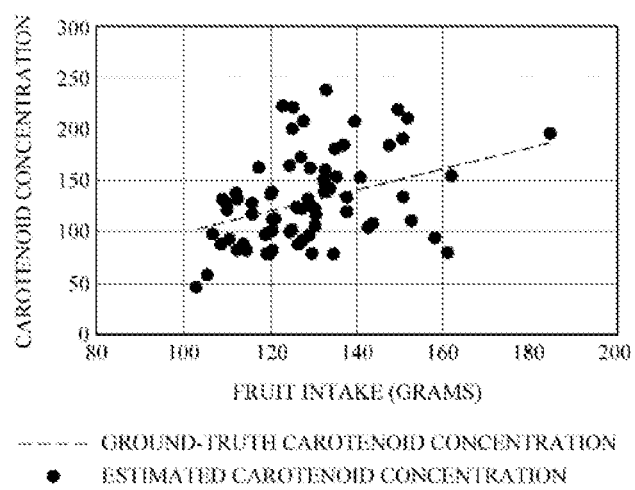
FIGS. 3A and 3B are graphs showing the correlation between personal information and carotenoid concentration.
Figure 3B:
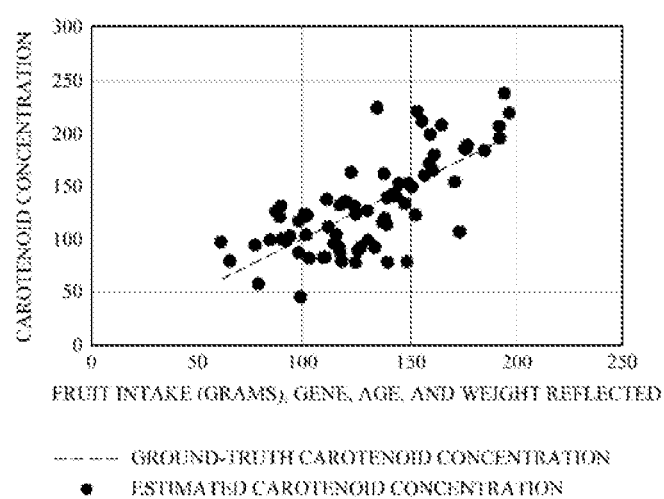

FIG. 3A shows the correlation between fruit intake and the carotenoid concentration, and FIG. 3B shows the correlation between values obtained based on fruit intake and personal information of genes, age, and weight through a machine learning method (e.g., multiple regression analysis) or a machine learning model, and the carotenoid concentration. The machine learning model may use the fruit intake and the personal information of genes, age, and weight as input parameters, and may obtain an estimated carotenoid concentration as output. The machine learning model may be trained to minimize a difference (i.e., loss) between the estimated carotenoid concentration and a ground-truth carotenoid concentration that is pre-stored in a system. The correlation between fruit intake and the carotenoid concentration is R=0.36 in FIG. 3A, and the correlation between the values obtained based on the fruit intake and the personal information of genes, age, and weight through multiple regress analysis and the carotenoid concentration is R=0.72 in FIG. 3B, and thus it can be seen that the correlation of FIG. 3B is higher than that of FIG. 3A. That is, when personal information associated with the antioxidant concentration is selected using multiple regression analysis, high correlation is achieved with antioxidant concentration, enabling more accurate measurement.

In addition, the processor 130 may output an interface to a display to receive direct input of the user's personal information associated with the antioxidant component from a user, may collect the user's personal information in conjunction with a health application installed in the electronic device, or may obtain the user's personal information from another electronic device through a communication module. For example, the physiological pattern information that may vary depending on the timing of measurement, for example, personal information such as the amount of alcohol intake, the amount of smoking, the amount of sleep, and the like, may be obtained by the processor 130 directly from the user through the display of the electronic device, and other physiological information, such as the amount of exercise, or the body information may be obtained by the processor 130 from other health applications installed in the electronic device for use by the user. When user information is generally stored in a medical institution, such as clinical information or genetic information, the processor 130 may obtain the user's personal information, for example, from the medical institution through a communication module.

In addition, the processor 130 may obtain the rate of utilization of an antioxidant component by using the obtained user's personal information, and the rate of utilization of an antioxidant component may be obtained based on the absorption rate or amount of consumption of the antioxidant component in the body.

Hereinafter, Equation 4 shows the concentration of an antioxidant component in the body, Equation 5 shows the absorption rate in the body, and Equation 6 shows the amount of consumption in the body.

$$SCS=[\{(\text{Iintake}-L1)\} \times AR-L2] \times AccR \quad (4)$$

$$AR=M \times G1 \times G2 \times P \quad (5)$$

$$L2=S+B \quad (6)$$

In Equation 4, SCS represents the concentration of carotenoids accumulated in the skin, Iintake represents food intake, L1 represents digestive loss, AR represents absorption rate in the body, L2 represents the amount of consumption in the body, and AccR represents skin storage rate. In Equation 5, M represents a type of gut microorganism, G1 represents the degree of genetic modification, G2 represents the level of gene expression, and P represents the amount of protein. In Equation 6, S represents the amount of oxidative stress from, for example, exercise amount, stress, and sleep pattern, and B represents body information, for example, the amount of body fat.

In general, carotenoids are not synthesized in the body and can be ingested through food, and the absorption rate AR of carotenoids present in the ingested food is related to genetic information and clinical information among the user's personal information, for example, information associated with types of gut microorganisms. For example, the absorption rate AR in the body may be determined based on the gut microorganism, the degrees of gene modification and expression, and the protein according to Equation 5. In addition, the consumption amount L2 of the absorbed carotenoids is related to personal body information or physiological pattern information among the user's personal information. For example, according to Equation 6, the consumption amount L2 of carotenoids may be determined by a linear combination between the amount of oxidative stress associated with the physiological pattern information and the amount of body fat, which is body information, or a classification model method thereof.

The processor 130 may determine each of the obtained absorption rate and/or consumption amount of antioxidant component in the body as the utilization rate of the antioxidant component, or may determine the utilization rate of the antioxidant component by using both the absorption rate and consumption amount in the body. In the case of using both the absorption rate and consumption amount in the body, for example, assuming that the user's carotenoid intake is 100 mg, the absorption rate is 70%, and the consumption amount is 30 mg, the amount of carotenoids stored in the body is obtained as 40 mg by subtracting the consumption amount of 30 mg from a value obtained by multiplying the carotenoid intake of 100 mg by the absorption rate of 70%. It can be seen that 40% of the carotenoid intake of 100 mg is stored, and hence the utilization rate of carotenoids can be determined as 60%. The method for determining the utilization rate in the body is not limited thereto.

In addition, the processor 130 may further obtain the required amount of the antioxidant component in the body by using the user's personal information associated with the concentration of the antioxidant component. The required amount in the body is related to the genetic information associated with the absorption rate in the body among the user's personal information or an initial value of the concentration of the antioxidant component in the body.

Figure 4A:
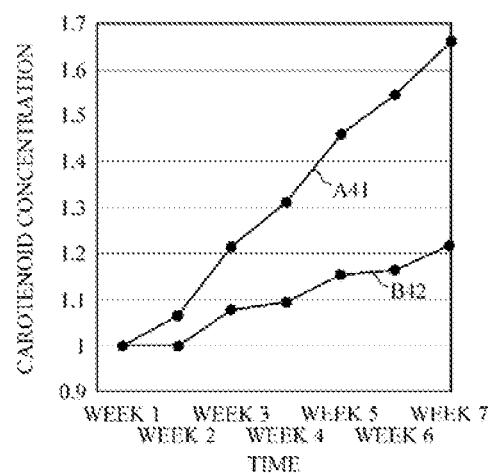
FIGS. 4A and 4B are diagrams for explaining the required amount of antioxidant component in the body.
Figure 4B:
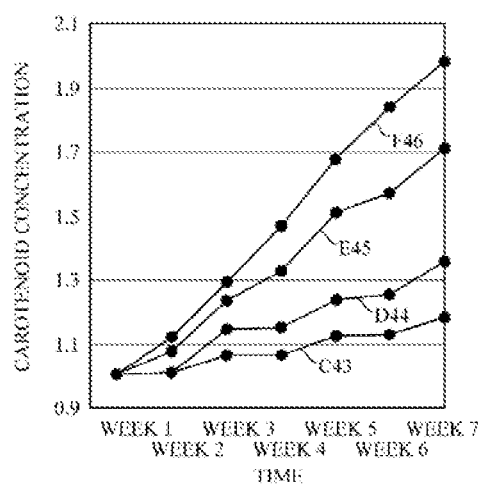

FIGS. 4A and 4B are diagrams for explaining the required amount of antioxidant component in the body. Referring to FIG. 4A, it is assumed that between A 41 and B 42 having genetic information associated with the absorption rate in the body, A 41 has the genetic information in which the absorption rate in the body is higher than that of B 42. If A 41 and B 42 are to eat the same amount of fruit at regular time intervals (e.g., weekly), the increase in skin carotenoid concentration of A 41 over time appears higher than that of B 42. Therefore, it can be seen that B 42, which has a low absorption rate and a small increase amount, requires a more amount of antioxidant component over time than A 41 having a high absorption rate and a large increase amount. Referring to FIG. 4B, it is assumed that C 43 has the highest initial value of the antioxidant component in vivo, followed by D 44, E 45, and F 46. If C 43, D 44, E 45, and F 46 are to eat the same amount of fruit at regular time intervals, the increase in skin carotenoid concentration appears high over time in the order of F 46, E 45, D 44, and C 43. Therefore, it can be seen that C 43, D 44, E 45, and F 46 require a more amount of antioxidant component over time in that order corresponding to the order of initial values of the antioxidant component.

The processor 130 may determine the required amount of the antioxidant component in the body based on at least one of the genetic information associated with the absorption rate in the body or the initial value of the concentration of the antioxidant component. For example, in a case in which stored carotenoids is 40 mg, 60 mg is consumed by exercise or the like, and the absorption rate is 70%, an additional intake of about 28 mg may be required. In this case, the processor 130 may increase the required amount higher than 28 mg or decrease the required amount lower than 28 mg by reflecting the initial value of the concentration of the antioxidant component in the body for each individual, and when the user has a gene with a low absorption rate in the body, the processor 130 may determine the required amount using a method of adding a weight to the usual required amount. The method by which the processor 130 determines the required amount of the antioxidant component is not limited thereto.

Then, the processor 130 may determine a user grade corresponding to the obtained body utilization rate or required amount of the antioxidant component, and may provide a health guideline to the user through the display 121 according to the determined user grade.

Table 2 below shows examples of user grades and health guidelines, and the grades and the guidelines are not limited thereto.

TABLE 2

| Grade | Health guidelines |
| --- | --- |
| A | Maintain the current status. There is no need to take additional nutritional supplements. |
| B | Try to eat 100 g or more of a variety of fruits and vegetables. |
| C | Try to eat 250 g or more of fruits and vegetables high in antioxidants. It is also recommended to take a nutritional supplement that contains 50% or more of the daily nutritional value. |
| D | Health management is required, and please try to improve the health by taking a nutritional supplement that contains 100% or more of the daily nutritional value. |

For example, if the percentage or utilization rate of the required amount in the body is less than 20% with 100% as the maximum limit, the processor 130 may determine grade A when 20% or less, grade B when 20% or more and less than 50%, grade C when 50% or more and less than 70%, and grade D when 70% or more, and may output a guideline through a display according to the determined user grade.

In addition, the processor 130 may classify a user type individually or according to the determined user grade, and output a health guideline, such as a diet suggestion, a life pattern suggestion, or the like, through the display 121 according to the classified user type. Table 3 below shows examples of classification according to user type, but the classification is not limited thereto. Here, the user type may be determined through classification technique using the user's personal information and the information on the measured concentration of the antioxidant component (e.g., utilization rate and the required amount). The classification technique may include various machine learning techniques, such as K-nearest neighbors (KNN), decision tree, random forest, naïve Bayes, gradient boosting algorithm, etc. Here, the diet suggestion may include nutritional supplements or user-customized diet, and the life pattern suggestion may include an exercise amount, a sleep pattern, a meal time, and the like.

TABLE 3

| Type | Definition | Health guidelines |
|---|---|---|
| Wellness | Type with higher nutritional indicators compared to other types | You are in very good health, and maintain the current status. There is no need to take additional nutritional supplements. |
| Diet | Type with lower nutritional indicators compared to other types | Nutritional management is needed, so try to eat a sufficient amount of vegetables and fruits. Take nutritional supplements for the deficient amount of nutrients. |
| Life pattern (Life Pattern) | Type with lower life pattern indicators compared to other types (E.g.,: Type with excessive exercise or too little exercise, type with irregular lifestyles, and type with high BMI) | A healthy life can be reinforced by avoiding excessive exercise and keeping a regular lifestyle. Weight management is needed for health care. |
| Stress | Type with higher nutritional indicators, higher life pattern indicators, and lower antioxidant indicators compared to other types or type with high stress indicators | Your diet and life pattern are well maintained, but stress management is needed for a healthy life. |

For example, the processor 130 may output the guideline of "Your diet and life pattern are well maintained, but stress management is needed for a healthy life." for the stress type through the display 121, may output the guideline of "Nutritional management is needed, so try to eat a sufficient amount of vegetables and fruits." for the diet type related to food intake through the display 121, and may output the guideline of "A healthy life can be reinforced by avoiding excessive exercise and keeping a regular lifestyle." for the life pattern type related to exercise through the display 121. The above classification is merely exemplary, and the present disclosure is not limited thereto.

According to another exemplary embodiment, the processor 130 may provide a health guideline to the user based on the estimated required amount of the antioxidant component. For example, when the required amount is less than or equal to a predetermined threshold, the processor 130 may provide a health guideline such as "eat more fruit" and "eat more vegetables" through the display.

In addition, according to another exemplary embodiment, the processor may provide a health guideline by using both an estimated utilization rate of the antioxidant component and the required amount of the antioxidant component. For example, when the utilization rate of the antioxidant component is 80% or more and the required amount of the antioxidant component is less than 100 mg, the processor 130 may provide a health guideline, such as "eat more fruit," through the display. The method of providing the health guideline using the required mount and utilization rate of the antioxidant component is not limited thereto.

In addition, the processor 130 may output notification information to the user using a sound output interface, a haptic device, and the like. A specific example of providing a health guideline using the display will be described in detailed below with reference to FIG. 6.

Figure 5:
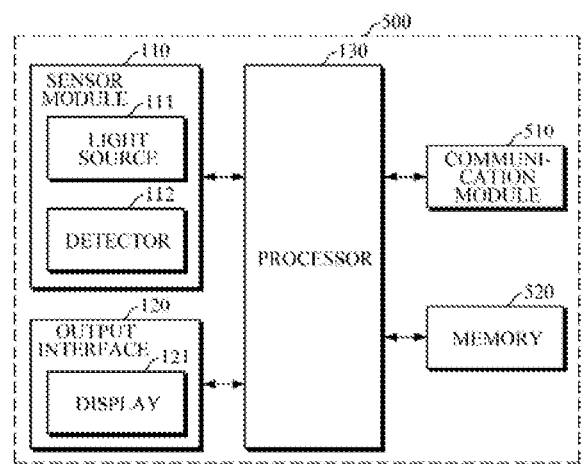
FIG. 5 is a block diagram illustrating an electronic device according to another exemplary embodiment.

FIG. 5 is a block diagram illustrating an electronic device according to another exemplary embodiment.

Referring to FIG. 5, an electronic device 500 may include a sensor module 110, an output interface 120, a communication module 510, and a memory 520. The sensor module 110, the output interface 120, and the processor 130 are described above, and hence detailed descriptions thereof will not be reiterated.

The communication module 510 may support the establishment of a direct (cable) communication channel and/or wireless communication channel between the electronic device 500 and another electronic device or server in a network environment or the sensor module and the communication therebetween through the established communication channel. The communication module 510 may be operated independently of the processor 130 and may include one or more communication processors that support direct communication and/or wireless communication. The communication module 510 may include a wireless communication module, such as, a cellular communication module, a short-range wireless communication module, a global navigation satellite system (GNSS) communication module, or the like, and/or a wired communication module, such as a local area network (LAN) communication module, a power line communication module, or the like. Such various types of communication modules may be integrated into a single chip, or may be implemented as a plurality of separate chips. The wireless communication module may verify and authenticate the electronic device 500 in a communication network using subscriber information (e.g., international mobile subscriber identity (IMSI), or the like) stored in a subscriber identity module.

For example, when the output interface 120 outputs the health guidelines, the communication module 510 may transmit data necessary to simultaneously output the health guidelines from an external device (e.g., a smartphone, a desktop PC), and may receive various data (e.g., user's personal information) related to the operation of the electronic device 500 from the external device.

The memory 520 may store driving conditions required for driving a sensor device and various data required by other components of the electronic device, for example, software and input data and/or output data for commands related to the software. For example, the memory 520 may store a variety of data, such as the estimated rate of utilization of the antioxidant component of a user, user type, health guidelines, user's personal information obtained from an external server.

The memory 520 may include a storage medium, such as a memory of flash memory type, hard disk type, multimedia card micro type, or card type (e.g., SD or XD memory), random access memory (RAM), static random access memory (SRAM), read-only memory (ROM), electrically erasable programmable read-only memory (EEPROM), programmable read-only memory (PROM), magnetic memory, magnetic disk, optical disk, or the like, but is not limited thereto.

Hereinafter, various embodiments of visually displaying health guidelines in the electronic device 100 and 500 will be described with reference to FIGS. 6 to 7E.

Figure 6:
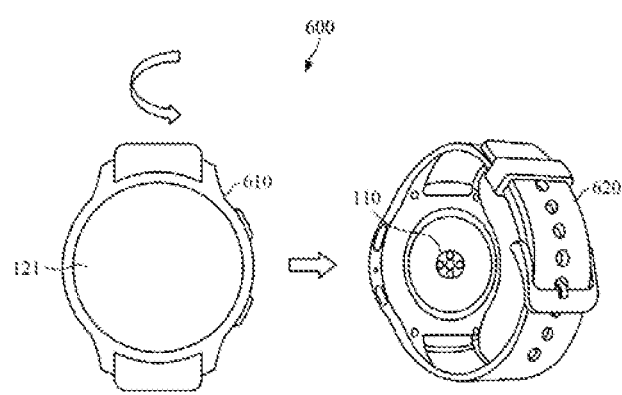
FIGS. 6 and 7A-7F are diagrams for explaining various embodiments of visually displaying health guidelines in an electronic device.

FIG. 6 illustrates a wearable device in the form of a smart watch as one embodiment of the electronic device 100 and 500 described above.

Referring to FIG. 6, a wearable device 600 may include a main body 610 and a strap 620. The main body 610 may form the outer appearance of the wearable device 600, and includes a display 121 on the front surface thereof as illustrated to display various information including time information, received message information, health guideline information, and the like. In addition, a sensor module 110 may be disposed on the rear surface of the main body 610.

Figure 7A:
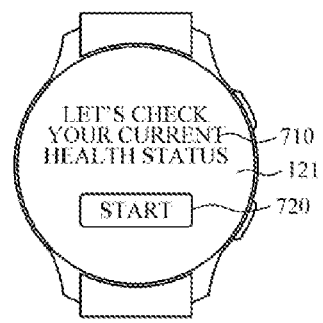
Figure 7B:
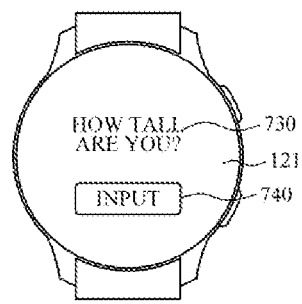
Figure 7C:
Figure 7D:
Figure 7E:

FIGS. 7A to 7C are diagrams for explaining an embodiment of visually providing health guidelines using a smart watch.

Referring to FIG. 7A, the processor 130 may display a start text message on the display 121. For example, as illustrated, the processor 130 may display on the display 121 a text message suggesting the user to provide health information, such as "Let's check your current health status" 170.

When the user touches "start" 720 as shown in FIG. 7A, the processor 130 may display on the display 121 a text message suggesting the user to input user's personal information as shown in FIG. 7B. For example, the processor 130 may display on the display a text message related to the body information of the user, such as "how tall are you?" 730, and the user may input the response by touching "input" 740. The user's personal information that can be input through the display 121 may include not only personal body information, such as height, weight, age, and the like, but also personal life information, such as stress index, an exercise amount, disease information, drinking, and smoking. The processor 130 may display a text message through the display 121 to obtain a variety of personal information, and the user may input the response through the display 121. Other than the case of the direct input by the user as described above, when the user's personal information is pre-stored in the electronic device, or for the user's personal information that can be obtained by the processor 130 in conjunction with other health applications or other devices (e.g., medical institution server), the operation shown in FIG. 7B may be omitted.

When the user touches "start" shown in FIG. 7A, the processor 130 may drive the sensor module 110 to obtain the concentration of the antioxidant component of the user, may obtain the utilization rate of the antioxidant component using the obtained concentration of the antioxidant component and the user personal information obtained through the display 121 or the like, and may provide the health guideline to the user using the obtained utilization rate of the antioxidant component.

FIGS. 7C to 7F show text messages related to the user's health guidelines that are finally displayed on the display 121 according to one exemplary embodiment.

For example, when the utilization rate or required amount of the antioxidant component is 20% or more and less than 50%, the processor 130 may output "Try to eat 100 g or more of a variety of fruits and vegetables," 750 which is the guideline for grade B, to the display 121 (see FIG. 7C). Also, when the user is classified as the stress type among the user types, the processor 130 may additionally output a text message of "your stress index is high" 760 (see FIG. 7D), and accordingly, the processor 130 may further output a text message of "Your diet and life pattern are well maintained, but stress management is needed for a healthy life" 770 (see FIG. 7E). The text messages related to the health guidelines displayed on the display 121 are not limited to the above examples.

Figure 7F:
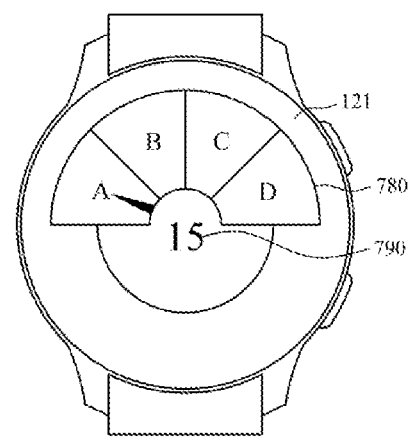

In addition, as shown in FIG. 7F, for example, various visual means, such as a pie chart 780 and/or text 790 indicating a percentage of the concentration or required amount of an antioxidant component, may be displayed on the display 121, so that the user can easily check the estimation result. Referring to FIG. 7F, the user's grade is A as indicated by an arrow and the percentage of the utilization rate or required amount of the antioxidant component is 15%. If the user touches A in the pie chart 780, the text messages of "Maintain the current status. There is no need to take additional nutritional supplements" may be further displayed on the display 121. However, the visual display method is not limited to the above examples.

Figure 8:
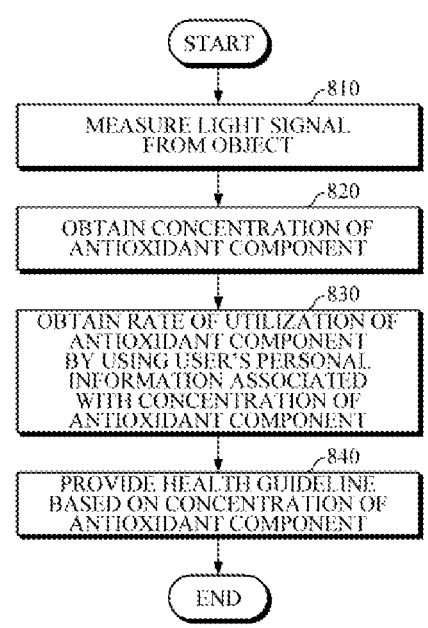
FIG. 8 is a flowchart illustrating a method of providing a health guideline according to an exemplary embodiment.

FIG. 8 is a flowchart illustrating a method of providing a health guideline according to an exemplary embodiment.

The method of FIG. 8 is an embodiment performed by the electronic device 100 and 500 according to the exemplary embodiments of FIGS. 1 and 5, which will be briefly described in order to avoid redundant description.

First, the sensor module of the electronic device may measure a light signal from an object in operation 810, and the processor may obtain the concentration of an antioxidant component based on the measured light signal in operation 820.

For example, the processor may input the light signal to a machine learning model that is trained to predict a carotenoid concentration based on input parameters that includes an amount of food consumption, an age, and a weight of the user, and may identify antioxidant level changes of the user based on an output signal of the machine learning model.

The electronic device may obtain a rate of utilization of the antioxidant component by using the user's personal information associated with the concentration of the antioxidant component in operation 830. The user's personal information associated with the concentration of the antioxidant component may include the user's genetic information, clinical information, physiological pattern information, or body information. The genetic information may include a gene associated with the concentration of the antioxidant component, the clinical information may include gut microbial information, the physiological pattern information may include stress, an exercise amount, sleep pattern, alcohol consumption, or smoking amount, and the body information may include gender, age, height, weight, or body composition. In this case, the electronic device may obtain the user's personal information associated with the concentration of the antioxidant component using a multiple regression analysis method, may receive the user's personal information directly from the user through an interface of the display, collect the user's personal information in conjunction with health applications installed in the electronic device, or collect the user's personal information from another electronic device through the communication module.

For example, the electronic device may obtain the concentration of the antioxidant component based on at least one of the absorption rate or amount of consumption of the antioxidant component by using the user personal information. In this case, the absorption rate of the antioxidant component may be determined based on the gut microorganisms, genes, or proteins, and the amount of consumption of the antioxidant component may be determined based on the physiological pattern information or the body information. The electronic device may determine that each of the obtained absorption rate of the antioxidant component in the body or the amount of consumption of the antioxidant component in the body is the rate of utilization of the antioxidant component, or may determine the rate of utilization of the antioxidant component by using both the absorption rate in the body and the amount of consumption in the body.

Then, the electronic device may provide a health guideline to the user based on the obtained rate of utilization of the antioxidant component in operation 840. For example, a user grade may be determined corresponding to the obtained rate of utilization of the antioxidant component, and the health guideline may be provided to the user through the display according to the determined user grade.

Figure 9:
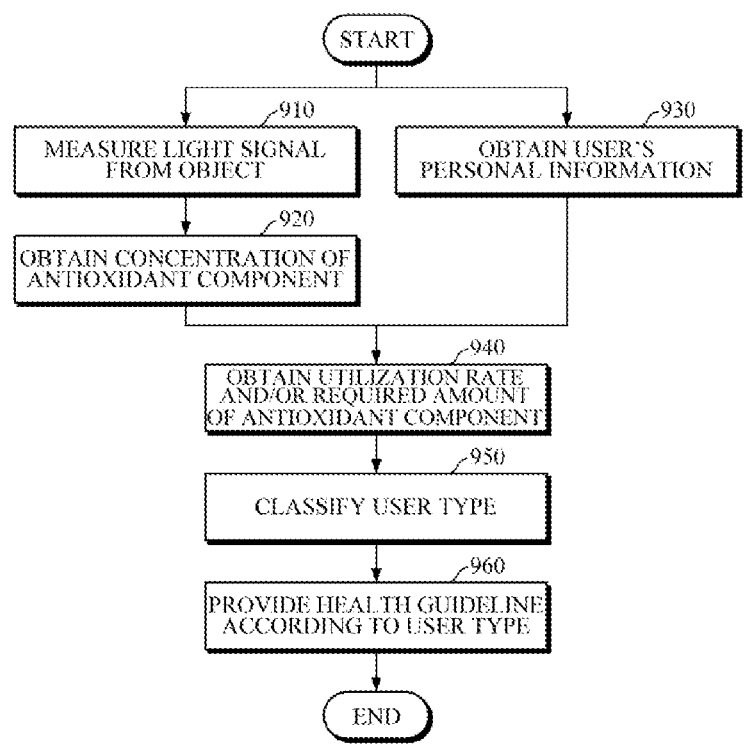
FIG. 9 is a flowchart illustrating a method of providing a health guideline according to another exemplary embodiment.

FIG. 9 is a flowchart illustrating a method of providing a health guideline according to another exemplary embodiment.

The method of FIG. 9 is an embodiment performed by the electronic device 100 and 500 according to the exemplary embodiments of FIGS. 1 and 5, which will be briefly described in order to avoid redundant description.

First, the sensor module of the electronic device may measure a light signal from an object in operation 910, and the processor may obtain the concentration of an antioxidant component based on the measured light signal in operation 920.

In addition, the processor may output an interface to the display to receive direct input of user personal information associated with the concentration of the antioxidant component from the user, may collect the user personal information in conjunction with health applications installed in the electronic device, or may obtain the user personal information from another electronic device through the communication module in operation 930.

Then, the electronic device may obtain a rate of utilization of the antioxidant component and/or the required amount of the antioxidant component in the body by using the user personal information in operation 940. At this time, the rate of utilization of the antioxidant component may be obtained based on the absorption rate or amount of consumption of the antioxidant component in the body. Further, the required amount in the body may be determined based on at least one of the genetic information associated with the absorption rate in the body or the initial value of the concentration of an antioxidant component.

Then, the electronic device may classify user types by using the user personal information and the information on the measured concentration of the antioxidant component, for example, the rate of utilization and/or the required amount in operation 950. At this time, the classification technique for the user types may include various machine learning techniques.

Then, the electronic device may provide a health guideline, such as a diet suggestion or a life pattern suggestion, according to the classified user type in operation 960. Here, the diet suggestion may include nutritional supplements or user-customized diet, and the life pattern suggestion may include an exercise amount, a sleep pattern, a meal time, and the like.

The current embodiments can be implemented as computer readable codes in a computer readable record medium. Codes and code segments constituting the computer program can be easily inferred by a skilled computer programmer in the art. The computer readable record medium includes all types of record media in which computer readable data are stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:
1. A watch comprising:
a main body;
a strap connected to the main body,
wherein the main body of the watch comprises:
an optical sensor disposed on a first surface of the main body and configured to measure a light signal from a user, wherein the optical sensor comprises a plurality of light sources positioned within a circular area and a plurality of detectors disposed on an outer side of the circular area;
a display disposed on a second surface of the main body and configured to provide an input interface;
a memory configured to store a mapping table in which user grades are mapped to corresponding carotenoid utilization rates, respectively, and
a processor configured to:
control the optical sensor to obtain an amount of the light signal measured at a plurality of wavelengths;
control the input interface to receive personal information comprising a body fat amount of the user;
obtain a concentration of carotenoids accumulated in a skin of the user based on a feature value representing an antioxidant peak by calculating absorbance values at the plurality of wavelengths of the light signal based on a ratio between the amount of light measured from the light signal at the plurality of wavelengths and a reference amount of light at the plurality of wavelengths, and obtaining the feature value representing the antioxidant peak by combining the absorbance values across the plurality of wavelengths;
obtain a utilization rate of the carotenoids by subtracting a consumption amount of the carotenoids in a body of the user that is obtained based on the body fat amount, from a product of an absorption rate and a difference between food intake and digestive loss; and provide a user grade corresponding to the utilization rate of the carotenoids of the user through the display based on the mapping table.

2. The watch of claim 1, wherein the processor is further configured to control the input interface to receive a user input for initiating a health status check, display a graphical pie chart illustrating a plurality of user grades, along with a mark indicating a specific user grade corresponding to the utilization rate of the carotenoids of the user, among the plurality of user grades, and present a numerical value corresponding to a position of the mark within the specific user grade, together with the graphical pie chart.

3. The watch of claim 1, wherein the processor is further configured to obtain the absorption rate of the carotenoids based on genetic information and clinical information of the user, and obtain the consumption amount of the carotenoids based on physiological pattern information and body information of the user, the genetic information comprises a gene associated with the concentration of the carotenoids, the clinical information comprises gut microbial information, the physiological pattern information comprises at least one of stress, exercise amount, sleep pattern, alcohol consumption, or smoking amount, and the body information comprises at least one of gender, age, height, weight, or body composition.

4. The watch of claim 3, wherein the personal information comprises the genetic information, the clinical information, the physiological pattern information, and the body information, and wherein the processor is further configured to select the personal information associated with the concentration of the carotenoids by using a machine learning method.

5. The watch of claim 1, wherein the processor is further configured to control the input interface to receive a direct input of the personal information associated with the concentration of the carotenoids from the user, collect the personal information in conjunction with a health application installed in the watch, or collect the personal information from an electronic device.

6. The watch of claim 1, wherein the processor is further configured to obtain the utilization rate of the carotenoids based on the absorption rate and the consumption amount of the carotenoids by using the personal information of the user associated with the concentration of the carotenoids.

7. The watch of claim 6, wherein the processor is further configured to determine the absorption rate of the carotenoids based on at least one of gut microorganisms, genes, or proteins, and determine the consumption amount of the carotenoids based on at least one of physiological pattern information or body information.

8. The watch of claim 1, wherein the processor is further configured to classify a user type according to the user grade and output at least one of a diet suggestion and a life pattern suggestion through the display according to the user type.

9. The watch of claim 8, wherein the diet suggestion comprises at least one of a nutritional supplement or a user-customized diet, and the life pattern suggestion comprises at least one of an exercise amount, a sleep pattern, or a meal time.

10. The watch of claim 1, wherein the processor is further configured to further obtain a required amount of the carotenoids by using the personal information of the user, and provide a health guideline to the user based on the utilization rate of the carotenoids and the required amount of the carotenoids.

11. A method of operating a watch comprising a main body and a strap connected to the main body, wherein the main body comprises an optical sensor, a display configured to provide an input interface, a memory configured to store a mapping table in which user grades are mapped to corresponding carotenoid utilization rates, respectively, and a processor, and wherein the method comprises:

measuring a light signal from a user by the optical sensor;

obtaining, by the processor, an amount of the light signal measured at a plurality of wavelengths;

controlling, by the processor, the input interface to receive personal information comprising a body fat amount of the user;

obtaining, by the processor, a concentration of carotenoids accumulated in a skin of the user based on a feature value representing an antioxidant peak by calculating absorbance values at the plurality of wavelengths of the light signal based on a ratio between the amount of light measured from the light signal at the plurality of wavelengths and a reference amount of light at the plurality of wavelengths, and obtaining the feature value representing the antioxidant peak by combining the absorbance values across the plurality of wavelengths;

obtaining, by the processor, a utilization rate of the carotenoids by subtracting a consumption amount of the carotenoids in a body of the user that is obtained based on the body fat amount, from a product of an absorption rate and a difference between food intake and digestive loss; and providing, by the display, a user grade corresponding to the utilization rate of the carotenoids of the user based on the mapping table.

12. The method of claim 11, further comprising:

obtaining the absorption rate of the carotenoids based on genetic information and clinical information of the user; and obtaining the consumption amount of the carotenoids based on physiological pattern information and body information of the user, the genetic information comprises a gene associated with the concentration of the carotenoids, the clinical information comprises gut microbial information, the physiological pattern information comprises at least one of stress, exercise amount, sleep pattern, alcohol consumption, or smoking amount, and the body information comprises at least one of gender, age, height, weight, or body composition.

13. The method of claim 12, wherein the personal information comprises the genetic information, the clinical information, the physiological pattern information, and the body information, and wherein the obtaining of the utilization rate of the carotenoids comprises selecting the personal information associated with the concentration of the carotenoids by using a machine learning method.

14. The method of claim 11, wherein the obtaining of the utilization rate of the carotenoids comprises receiving a direct input of the personal information associated with the concentration of the carotenoids from the user, collecting the personal information in conjunction with a health application installed in the watch, or collecting the personal information from an electronic device.

15. The method of claim 11, wherein the obtaining of the utilization rate of the carotenoids comprises obtaining the utilization rate of the carotenoids based on the absorption rate and the consumption amount of the carotenoids by using personal information of the user associated with the concentration of the carotenoids.

16. The method of claim 15, wherein the absorption rate of the carotenoids is determined based on at least one of gut microorganisms, genes, or proteins, and the consumption amount of the carotenoids is determined based on at least one of physiological pattern information or body information.

17. The method of claim 11, further comprising:
classifying a user type according to the user grade; and
outputting at least one of a diet suggestion and a life pattern suggestion through the display according to the user type.

18. A non-transitory computer-readable storage medium storing a program that is executable by a computer to perform a method of providing operating a watch comprising a main body and a strap connected to the main body,
wherein the main body comprises an optical sensor, a display configured to provide an input interface, a memory configured to store a mapping table in which user grades are mapped to corresponding carotenoid utilization rates, respectively, and a processor, and
wherein the method comprises:
obtaining an optical signal from a user by the optical sensor;
obtaining, by the processor, an amount of the light signal measured at a plurality of wavelengths;
controlling, by the processor, the input interface to receive personal information comprising a body fat amount of the user;
obtaining, by the processor, a concentration of carotenoids accumulated in a skin of the user based on a feature value representing an antioxidant peak by calculating absorbance values at the plurality of wavelengths of the optical signal based on a ratio between the amount of light measured from the optical signal at the plurality of wavelengths and a reference amount of light at the plurality of wavelengths, and obtaining the feature value representing the antioxidant peak by combining the absorbance values across the plurality of wavelengths;
obtaining, by the processor, a utilization rate of the carotenoids by subtracting a consumption amount of the carotenoids in a body of the user that is obtained based on the body fat amount, from a product of an absorption rate and a difference between food intake and digestive loss; and
providing, by the display, a user grade corresponding to the utilization rate of the carotenoids of the user based on the mapping table.

* * * * *